US006372259B1

(12) United States Patent
Kumar

(10) Patent No.: US 6,372,259 B1
(45) Date of Patent: Apr. 16, 2002

(54) PALATABLE, SUSTAINED RELEASE DRUG GRANULES

(75) Inventor: Vijay Kumar, Coralville, IA (US)

(73) Assignee: University of Iowa Research Foundation, Iowa, IA (US)

( * ) Notice: Subject to any disclaimer, the term of this patent is extended or adjusted under 35 U.S.C. 154(b) by 0 days.

(21) Appl. No.: 09/437,449

(22) Filed: Nov. 10, 1999

(51) Int. Cl.$^7$ .............................. A61K 9/14; A61K 9/50
(52) U.S. Cl. ....................................... 424/497; 424/489
(58) Field of Search ................................. 424/489, 497

(56) References Cited

U.S. PATENT DOCUMENTS 6,120,802 A * 9/2000 Breitenbach et al. ....... 424/464

OTHER PUBLICATIONS

Chem. Ab. 112:125055 1989.*
Physicians Desk Reference 54th Ed. "Motrin 1B".*
Chem. Pharm. Bull 37(5) 1366–1368 (1998) vol. 37, No. 5; Takayama et al.
Chem. Pharm. Bull 38(7) 1993; Takayama et al.
Drug Development and Industrial Pharmacy, 20(3), 315–325 (1994); Gupta et al.
Sci. Pharm. 49, 427–434 (1981); Elgindy et al.
Chem. Pharm. Bull. 43(6) 988–993 (1995); Sekizaki et al.
Chem. Pharm. Bull. 35(12) 4921–4927 (1987); Takayama et al.
J. Pharm. Pharmacol. 1983, 35: 341–344; Porter et al.

* cited by examiner

Primary Examiner—Thurman K. Page
Assistant Examiner—S. Howard
(74) Attorney, Agent, or Firm—McKee, Voorhees & Sease, P.L.C.

(57) ABSTRACT

A means and method for manufacturing palatable drug granules using a polymer having at least one free carboxyl group and PVP is described. This is achieved by (1) dissolving/suspending a drug in an aqueous solution of polymers and subsequently adjusting the pH of the solution to an acidic pH or (2) suspending a drug in an organic solution of one of the aforementioned polymers and then adding the other polymer solution, with constant agitation. The polymers form a complex and consequently entraps the drug and produce palatable drug granules that are suitable for preparing sustained release pharmaceutical dosage forms (powders, suspension, tablets, chewable tablets).

14 Claims, 6 Drawing Sheets

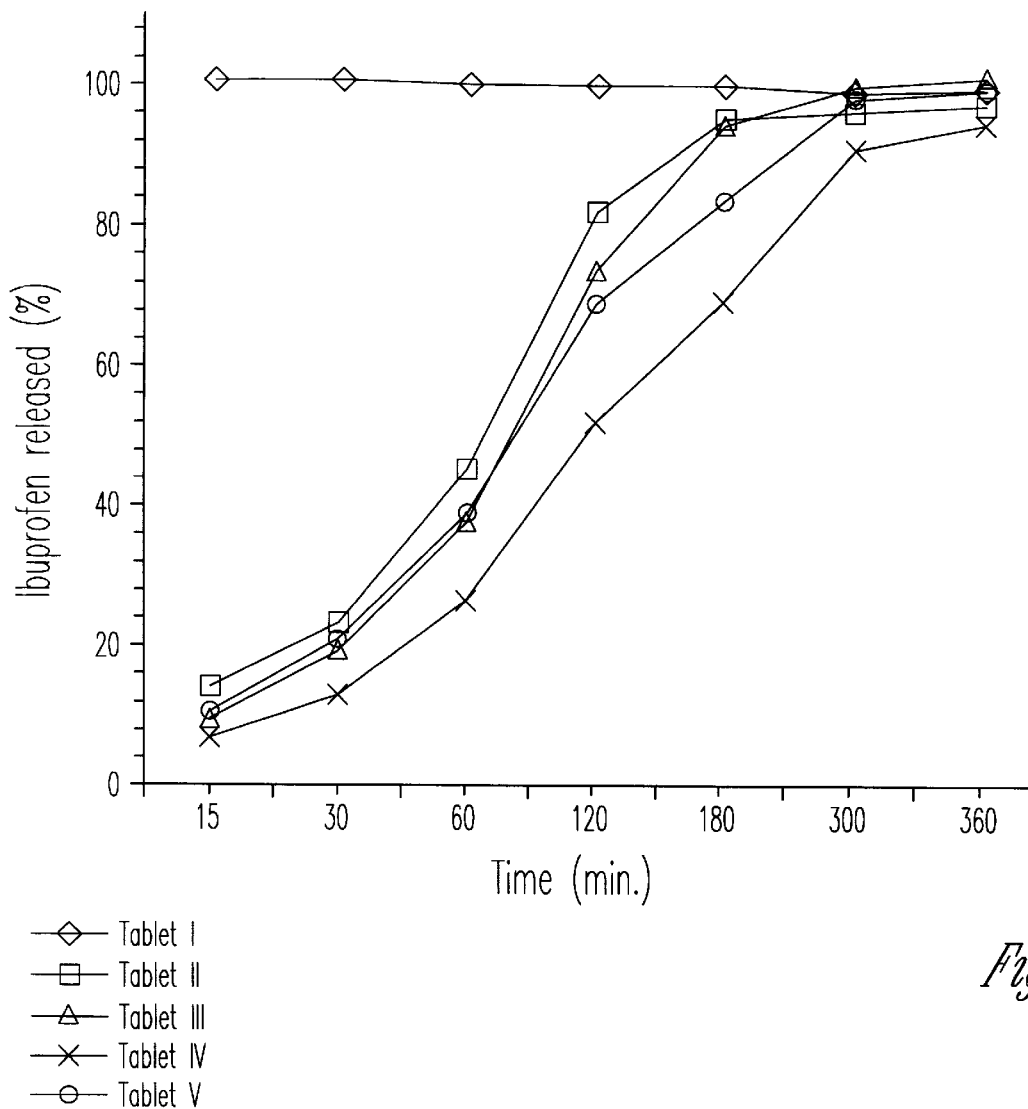

PALATABLE, SUSTAINED RELEASE DRUG GRANULES

FIELD OF THE INVENTION

This invention relates to a composition and method for producing palatable drug granules suitable for use in the development of pharmaceutical dosage forms. Specifically, this invention relates to the entrapment of drugs using a combination of polymer ingredients, and especially polyvinylpyrrolidone (PVP) and polyvinyl acetate phthalate (PVAP).

BACKGROUND OF THE INVENTION

For many people, taking medicine can be a very unpleasant experience. Tablets are the most commonly and widely used dosage form. Most tablet products are designed to be swallowed whole. This poses a serious problem in children and elderly patients who have difficulty swallowing. In addition, the drugs used in the tablets often have an offending taste.

Crushing of such tablets, for ease of swallowing, can cause significant changes in the bioavailability of the drug and may irritate the mucous membranes of the esophagus and stomach. Further, drugs sensitive to gastric fluids may degrade, or react with the gastric milieu, and produce potentially harmful byproducts.

Chewable tablets and liquids provide alternatives for people who are unable or unwilling to swallow pills. In most cases, however, chewable tablets and liquids are just as unpleasant tasting as pills. This makes it especially difficult for convincing small children to take their medicine, which is problematic if the medicine is necessary to treat an infection or other illness.

Chewable tablets are intended to be masticated in the mouth before swallowing. Thus, it must impart good flavor and mouth-feel. This presents a challenge to a formulator if the drug to be used is bitter in taste. Conventional methods of taste masking of such drugs with sweeteners or commonly used flavoring agents have not proven to be adequate, however.

To overcome this problem, several drug coating methods have been developed. Sugar coating is regarded as the oldest method for masking the taste of drug particles, and involves the deposition of sucrose using an aqueous solution. Sugar-coating has the disadvantages of requiring large quantities of coating material to be applied, and nonuniform distribution of the coating material. In addition, sugar coatings are generally not adequate to alleviate the foul taste of the medication.

Other taste-masking methods include: (a) coating of drug particles with a taste-neutral polymer by spray-drying, wet granulation, fluidized bed, and microencapsulation; (b) coating with molten waxes of a mixture of molten waxes and other pharmaceutical adjuvants; (c) entrapment of drug particles by complexation, flocculation or coagulation of an aqueous polymeric dispersion; (d) preparation of drug-cyclodextrin inclusion complexes; (e) adsorption of drug particles on resin and inorganic supports, and (f) solid dispersion methods wherein a drug and one or more taste neutral compounds are melted and cooled, or co-precipitated by a solvent evaporation technique. While these methods claim to have alleviated the deficiencies associated with taste-masking, there is a need in the art for a means of producing pharmaceutical products that overcomes the taste of bitter drugs.

Polymers have been used in the design and development of pharmaceutical products in order to modify the release pattern of the drug. Sustained or controlled release products are primarily developed to extend the release of a drug over a long period of time. Such preparations eliminate the need for multiple dosage regimens, especially for drugs requiring reasonably constant blood levels over a long period of time. Sustained release formulations have also been used frequently with drugs where rapid release is likely to cause undesirable side effects, such as the ulceration of the stomach commonly associated with potassium chloride and non-steroidal anti-inflammatory drugs. Other materials that have been commonly used in the manufacture of sustained released formulations include mixtures of waxes, shellac, etc.

It is not uncommon to use two or more polymers in a pharmaceutical preparation to develop a pharmaceutically acceptable product. However, the varied structure and chemistry of various polymers may render ample opportunity for them to undergo physical and/or chemical interaction in situ. Such interactions greatly influence product stability, modify drug release kinetics, alter drug bioavailability, and/or pose safety concerns.

For example, Satoh et al. Factors affecting the bioadhesive property of tablets consisting of hydroxypropyl cellulose and carboxyvinyl polymer. Chem. Pharm. Bull., 37, 1366–1368 (1989) reported that the use of a 3:2 weight ratio of hydroxylpropylcellulose (HPC) and carboxylvinyl polymer (CP) as excipients in tablets significantly decreased the bioadhesion force and greatly affected the drug release. Similar effects were noted by Takayama et al. Effect of interpolymer complex formation on bioadhesive property and drug release phenomenon of compressed tablet consisting of chitosan and sodium hyaluronate. Chem. Pharm. Bull., 38, 1993–1997 (1990) with compressed tablets prepared using chitosan and sodium hyaluronate. Tablets prepared using chitosan alone exhibited weak bioadhesive strength, whereas sodium hyaluronate and chitosan produced tablets with strong adhesive forces. The release of brilliant blue varied with the weight ratios of the two polymers, suggesting the occurrence of an interaction between sodium hyaluronate and chitosan.

Recently, the interaction of CP with HPC and sodium carboxymethylcellulose (NaCMC) and its effects on the bioadhesive strength and the release of verapamil was reported (Gupta et al., Interpolymer complexation and its effect on bioadhesive strength and dissolution characteristics of buccal drug delivery. Drug Dev. Ind. Pharm., 20, 315–325 (1994)). CP reportedly formed a stronger complex with HPC than with NaCMC.

Polyvinylpyrrolidone (PVP) is a water soluble, physiologically inert polyamide polymer. It exhibits unusual colloidal and complexing properties, and has been extensively used in pharmacy for various purposes.

Elgindy and Elegakey ─( Carbopol-polyvinypyrrolidone flocculation. Sci. Pharm., 49, 427–434 (1981)─ and Elegakey and Elgindy ─( Drug encapsulation by carbopol-polyvinylpyrrolidone flocculation technique, Sci. Pharm., 49, 434–441 (1981) prepared PVP-polyacrylic acid (Carbopol 934, 940, and 941) complexes and demonstrated their use in the development of sustained release drug products.

Further, Takayama and Nagai, Application of interpolymer complexation of polyvinylpyrrolidone/carboxyvinyl polymer to control of drug release. Chem. Pharm. Bull, 35, 4921–4927 (1987), reported that PVP forms a 1:1 complex with carboxyvinyl polymer. Recently, Gupta et al., Interpolymer complexation and its effect on bioadhesive strength and dissolution characteristics of buccal drug delivery. Drug Dev. Ind. Pharm., 20, 315–325 (1994)) reinvestigated the interaction between Carbopol 934 and PVP. The degree of complexation was found to be higher at low acidic conditions, and decreased with increasing pH of the solution. Compared to the parent polymers, the complex exhibited increased bioadhesive strength and decreased drug release rates.

More recently, Bell and Peppas, Swelling/syneresis phenomena in gel-forming interpolymer complexes. J. Biomater. Sci., Polym. Ed., 7, 671–83 (1996) studied the interaction of poly(methacrylic acid)(PMMA) with polyethylene glycol. They reported that complexation occurred at pH low enough to protonate the acid of PMMA. At high pH, the acid group becomes neutralized and, consequently, no complexation occurs.

While it has been known that PVP forms complexes with many substances, it was not known in the art that PVP reacts and forms a complex with polyvinyl acetate phthalate (PVAP), methacrylic acid-alkylmethacrylate copolymers (where alkyl=methyl, ethyl, etc.), and other acrylic and nonacrylic polymers having at least one free carboxylic group. The present inventor has now discovered that PVP readily reacts with PVAP, methacrylic acid-alkylmethacrylate copolymers (where alkyl=methyl, ethyl, etc.), and other acrylic and nonacrylic polymers having at least one free carboxylic group to form an insoluble complex. This complex can be used to produce highly palatable granules for bitter tasting drugs, and further serves as a sustained release effector.

Accordingly, it is a primary objective of the present invention to provide a composition and method for entrapping bitter-tasting drugs that results in a pharmaceutical dosage form that is palatable.

It is a further objective of the present invention to provide a composition and method for producing palatable granules of bitter-tasting drugs that provides a good mouth feel.

It is still a further objective of the present invention to provide a composition and method for entrapment of bitter-tasting drugs that may be used to prepare oral dosage forms, including tablets, chewable tablets, and suspensions.

It is yet a further objective of the present invention to provide a composition and method for preparing granules of bitter-tasting drugs which may be used to produce a sustained release product.

It is still a further objective of the present invention to provide a composition and method for the manufacture of palatable granules of bitter-tasting drugs which is cost-effective.

The method and means of accomplishing each of the above objectives as well as others will become apparent from the detailed description of the invention which follows hereafter.

SUMMARY OF THE INVENTION

The invention describes a method and composition for entrapping drugs that are bitter-tasting and/or require sustained-release properties. It uses an amorphous polymer complex consisting of PVAP, methacrylic acid-alkylmethacrylate copolymers (where alkyl=methyl, ethyl, etc.), or an acrylic or nonacrylic polymer having at least one free carboxylic group and polyvinylpyrrolidone (PVP) that is insoluble in acidic pH solutions or organic solvents in which the parent polymers dissolve. The entrapment is achieved by in situ complexation between the polymers in an organic solvent or acidic aqueous solution.

The in situ complexation between the polymers entraps the bitter tasting drug, providing a highly palatable powder dosage form that effectively eliminates the bitter taste of the drug and provides a good mouth-feel. The entrapment further provides a slower release profile for the encapsulated drug, thereby resulting in a sustained release dosage form. The palatable drug granules of this invention may be used to produce other oral dosage forms including tablets, effervescent tablets, chewable tablets and suspensions. Palatable powder, effervescent tablet, chewable tablet, and suspension dosage forms are an ideal alternative for geriatric, pediatric, and other patients who must take several pills a day.

BRIEF DESCRIPTION OF THE DRAWINGS

FIG. 6 shows release profiles of ibuprofen from various chewable tablet formulations in pH 7.4 phosphate buffer.

DETAILED DESCRIPTION OF THE PREFERRED EMBODIMENT

Figure 1:
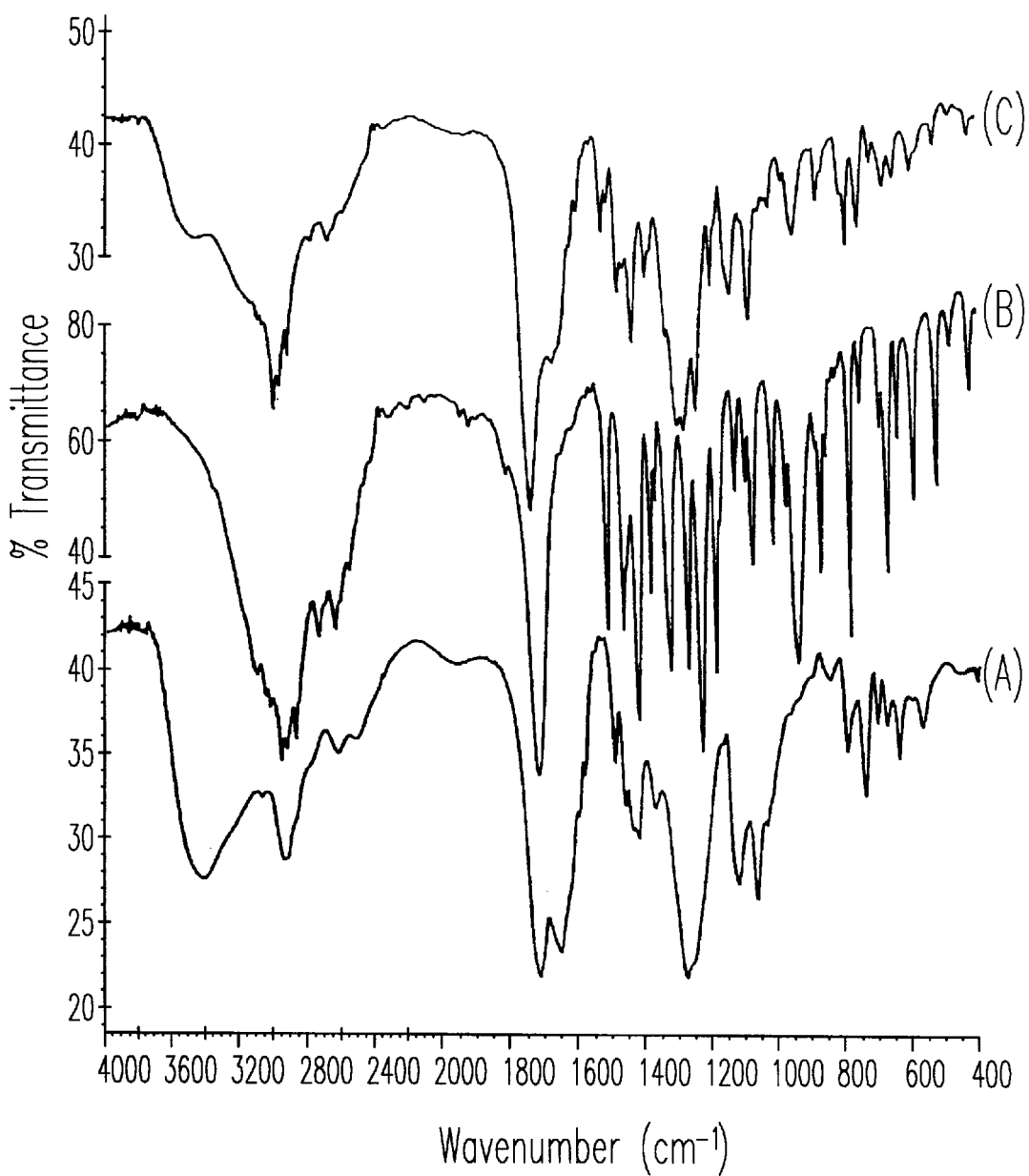
FIG. 1 shows FT-IR spectra of (A) PVAP-PVP complex, (B) ibuprofen, and (C) PVAP-PVP entrapped ibuprofen granules.

The present invention relates to the development of a new method to entrap drugs to produce palatable sustained release granules of bitter-tasting drugs using PVAP, methacrylic acid-alkylmethacrylate copolymers (where alkyl=methyl, ethyl, etc.), or an acrylic or nonacrylic polymer having at least one free carboxylic group and PVP.

Non-steroidal anti-inflammatory drugs (NSAIDs), such as ibuprofen, used as a model drug to demonstrate the art of this invention, are widely used in the treatment of painful musculoskeletal conditions. According to a recent report, more than 1% of the population of the United States use an NSAID daily. A large percentage of these patients are elderly people being treated for arthritis. The regimen for treating arthritis may require the patient to take an NSAID up to four times daily. Obviously, if the patient has difficulty swallowing pills, treatment of the disease can prove difficult. While some NSAIDs are available in a suspension dosage form for adults, the taste of the suspension is usually disagreeable.

Ibuprofen is also frequently used in small children to treat aches and pains and to lower fevers associated with infection. Since children are often unable to swallow pills, they will usually obtain ibuprofen in the form of a chewable tablet or a suspension. Again, however, the children will frequently refuse to take chewable tablets and/or suspensions due to their poor taste.

The present invention is predicated upon the discovery that PVAP, methacrylic acid-alkylmethacrylate copolymers (where alkyl=methyl, ethyl, etc.), or an acrylic or nonacrylic polymer having at least one free carboxylic group and PVP can be dissolved in organic solvents or alkaline aqueous solutions and mixed in different ratios to form an insoluble, amorphous complex that may be used to entrap drugs, especially bitter-tasting drugs. The complex is insoluble in aqueous acidic solutions, but dissolves readily in alkaline media. Reacidification of the alkali solution yields the same polymer complex. The complex effectively entraps the drug to produce palatable granules of bitter tasting drugs.

It has also been discovered that the entrapment method of this invention causes the drug to be released over a sustained period of time. Chewable tablets demonstrate little or no drug release in acidic environments (i.e. the stomach), and sustained release of the drug in a neutral to basic environment, such as that of the small intestine. This property of the dosage form enables the patient to take fewer doses of medication, and also protects against gastric irritation by preventing release of the drug in the stomach. This feature of the polymer entrapment is especially desirable with respect to drugs that are known gastric irritants, such as NSAIDs, antibiotics, and steroidal drugs.

As set forth above, the entrapment method of this invention involves a complex formed between two polymers, namely PVP and PVAP, methacrylic acid-alkylmethacrylate copolymers (where alkyl=methyl, ethyl, etc.), or an acrylic or nonacrylic polymer having at least one free carboxylic group. Various grades of PVP are commercially available, and all of these grades are appropriate for use in the invention.

The other acrylate and nonacrylate ingredients in the complexation process of this invention is a polymer having at least one free carboxylic group. Such polymers are readily ascertainable in the art and include but are not limited to acrylic polymers and copolymers, methacrylic acid polymer and copolymers, polyvinyl acetate phthlate (PVAP), cellulose acetate phthalate, cellulose acetate succinate, cellulose acetate trimellitate, methacrylic acid-alkylmethacrylate copolymers (where alkyl=methyl, ethyl, etc.), oxidized polysaccharides such as starch, cellulose, dextran, etc., carragenan, guar gum, chitin, hyaluronic acid, gellan, acacia, alginic acid, pectin, tragacanth, xanthan gum, sodium alginate, and sodium carboxymethylcellulose. The most preferred polymer for this purpose is PVAP.

PVAP is an enteric polymer commonly and widely used in film coatings of tablets. PVAP films have been reported to be much less permeable to water vapor and simulated gastric fluid than those prepared from other enteric polymers, such as cellulose acetate phthalate and hydroxypropylmethylcellulose phthalate. S. C. Porter, Effect of additives on the properties of an aqueous film coating. Pharm Tech., 4, 67–75 (1980). PVP, in contrast, is a water soluble, physiologically inert polyamide polymer. C. M. Adeyeye, et al., Anal. profiles of drug substances and excipients, 22, 555–685 (1993). It exhibits unusual colloidal and complexing properties, and has been extensively used in pharmacy as a protective colloid, viscosity-enhancing agent, solubility promoter, granulating/tabletting agent, and film forming material.

The structures of PVAP (a) and PVP (b) are set forth below:

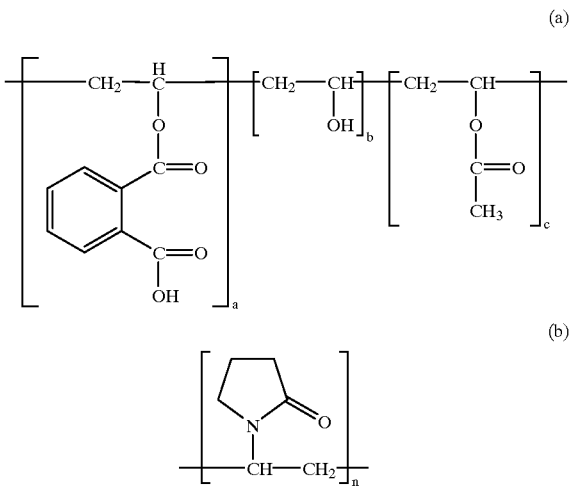

Unlike the parent polymers, the polymer complex is practically insoluble in common organic solvents (e.g., ethanol and acetone) but dissolves in dimethylformamide, dimethylsulfoxide, and a 4:1 (v/v) mixture of methylene chloride and methanol. The apparent pKa of the complex, as determined by Gran's method (Gran, Analyst, 77, 661–71 (1952)) is 3.85. It completely dissolves at a pH of about 5.8.

Studies indicate that the interaction between the free-carboxyl polymer and PVP initially involves the formation of hydrogen bonds between carbonyl groups of PVP and carboxylic groups of the other polymer at some point of the polymer chains. This makes the hydrophilic parts of the two flexible polymer chains strongly hydrophobic, causing the polymer chains to coil up into a compact structure and, consequently, precipitate out from the solution as an insoluble solid.

The polymer complex may be formed by combining various ratios of PVP and free-carboxyl polymer in an aqueous alkaline solution or an organic solvent. The drug to be entrapped in the polymers must be insoluble in the organic solvent used to dissolve the free-carboxyl polymer and PVP or soluble or suspendable in the aqueous alkaline solution. Such drugs are readily ascertainable by those skilled in the art, and their properties are described in various drug references, including Remington's Pharmaceutical Sciences, the Merck Index, AHFS Drug Information, American Society of Health System Pharmacists (1999), and the USPDI, the disclosures of which are hereby incorporated by reference. Appropriate drug classes for this purpose include, but are not limited to:

Anti-infective agents, including anthelmintics, antibiotics, antituberculosis agents, antivirals, quinolones, sulfonamides, and urinary anti-infectives;

Antineoplastic agents;

Autonomic drugs, including parasymphathomimetic (cholinergic) agents, anticholinergic agents, sympathomimetic (adrenergic) agents, and sympatholytic (adrenergic blocking) agents;

Blood formation and coagulation agents, including anti-enemia drugs, coagulants, anticoagulants, and thrombolytic agents;

Cardiovascular drugs, including cardiac drugs, antilipemic agents, hypotensive agents, and vasodilating agents;

Central nervous system agents, including analgesics and antipyretics, opiate antagonists, anticonvulsants, psychotherapeutic agents, anxiolytics, sedatives, hypnotics, and antimanic agents;

Electrolytic, caloric and water balance agents, including potassium-removing resins, diuretics, and uricosuric agents;

Antitussives, expectorants, and mucolytic agents;

Gastrointestinal drugs, including antacids and adsorbents, antidiarrhea agents, cathartics, laxatives, cholelitholytic agents, emetics, and antiemetics;

Hormones and synthetic substitutes, including adrenals, contraceptives, estrogens, antidiabetic agents, progestins, thyroid and antithyroid agents;

Smooth muscle relaxants;

Vitamins; and

Unclassified therapeutic agents, such as antigout agents, antiparkinsonian agents, bromocriptine mesylate, cromolyn sodium, and cyclosporine.

The drug is added to the solution after the polymers have already been dissolved.

The polymer with free carboxyl groups and PVP can be reacted in different weight ratios to produce the complex. However, it is preferred to use the ratio that affords the highest yield of the complex. Such weight ratios can be readily ascertained by those skilled in the art and will depend on the physical/chemical/structural properties of the particular polymer used. With respect to the preferred complex of PVAP/PVP, Appropriate ratios range from about 4:1 to about 1:4 by weight. A 2:1 ratio of PVAP to PVP has been shown by the inventor to provide the highest yield of the complex.

First, the polymers or the complex may be dissolved in an aqueous alkaline solution. The only requirement of the alkaline solution is that it be compatible with the other ingredients of the formulation. Examples of appropriate alkaline solutions that can be used to dissolve the free-carboxyl polymer include, but are not limited to, dilute and concentrated solutions of sodium hydroxide, potassium hydroxide, and ammonium hydroxide. Ammonium hydroxide is the preferred alkaline solution. The polymer containing the free carboxylic group(s) is dissolved in the alkaline solution and PVP in water, preferably by stirring or other agitational means, and then combined and the pH of the mixture is adjusted to about 4 or less to produce the complex.

In the alternative, the polymer with the free carboxylic group(s) and PVP may be dissolved in an organic solvent, or a mixture of organic solvents, separately, in which the drug is insoluble. Examples of appropriate organic solvents include, but are not limited to, methanol, ethanol, propylene glycol, glycerin, acetone, halogenated solvents, acetone, or a mixture thereof. The only requirement for the organic solvent is that it be capable of dissolving the free carboxylic polymer and PVP.

The drug is then added to the organic solvent or alkaline solution containing the polymers. Any drugs that are insoluble in the organic solvent or soluble/suspendable in the aqueous alkaline solution but precipitates in aqueous acidic solutions may be used.

In this invention, ibuprofen was used as an example to illustrate the effectiveness of the entrapment to produce palatable drug granules. Ibuprofen is a bitter-tasting, weakly acidic ($pK_a$ 5.2) nonsteroidal anti-inflammatory drug with a half-life of 1.8 to 2 hours. The ibuprofen or other drug is dissolved in the alkaline solution. The polymer complex can effectively entrap over 50% of the drug by weight. It is possible, however, that higher drug concentrations will reduce the ability of the complex to mask the taste of the drug. For this reason, the preferred concentration of drug in the polymer complex is about 40% or less by weight.

The pH of the solution is then slowly reduced to an acidic range. The pH of the solution is preferably lowered to a pH of 3 or less, depending on the pKa of the drug. The low pH of the solution ensues complexation between the free-carboxyl polymer and PVP, concomitant with the precipitation and subsequent entrapment of the drug, producing an insoluble product. The pH is lowered through the use of an acidic solution, which may consist of any acidic solution which is compatible with the drug. A preferred acidic solution for this purpose is dilute HCl. However, other concentrated and diluted acidic solutions may be appropriately used for this purpose.

The precipitated drug granules are then preferably filtered from the solution, washed with water, and vacuum dried. The entrapped drug granules can then be used as is or formulated into a tablet, capsule, or chewable tablet dosage form. Alternatively, the entrapped powder may be dispersed in water or other pharmaceutically acceptable dispersing medium prior to administration.

The invention also contemplates that addition of one or more various pharmaceutical excipients, including binders, fillers, lubricants, disintegrants, coloring agents, etc. to the formulation. Such excipients are well known and may be readily ascertained by those skilled in the art. The only requirement for the excipient(s) is that it be compatible with the other ingredients of the formulation.

If no flavoring agents are added to the polymer complex described above, the entrapped granules will be taste neutral or mild acidic. However, if for example, the granules are to be placed in a chewable tablet or developed into a suspension dosage form, it may be desirable to include a flavoring agent in the formulation. Any commercially available liquid or dry flavoring agent can be used. The liquid flavoring agent can also be adsorbed on the polymers of this invention or other polymers accepted for use in pharmaceutical preparations. Examples of appropriate flavoring agents include, but are not limited to, acacia syrup, anise oil, cherry syrup, ethyl vanillin, lemon oil, orange oil, peppermint water. The flavoring agent is preferably included in a range of from about 0.1–5.0% by weight of the formulation.

The resulting drug granules of the present invention are insoluble in acidic pH solutions. The entrapped drug granules of this invention are also palatable to the patient and provide a good mouth-feel, thereby providing an ideal alternative to conventional tablet dosage forms for geriatric, pediatric, and other patients who take several pills a day. Further, the preparation of granules is simple and economical to make.

The following examples are offered to illustrate but not limit the invention. Thus, they are presented with the understanding that various formulation modifications as well as method of delivery modifications may be made and still be within the spirit of the invention.

EXAMPLE 1

Preparation of Palatable PVAP-PVP Entrapped Ibuprofen Granules

Materials

PVAP (Lot No. 3665-B) and PVP-K90 (Lot No. 63) were received from Colorcon Inc. (West Point, Pa., USA) and International Specialty Products (Wayne, N.J., USA), respectively. All other chemicals were reagent grade and used as received. Ibuprofen, USP was purchased from Spectrum Chemical Mfg. Corp. (New Brunswick, N.J.). The cherry-flavored chewable tablet excipient was obtained as a gift from CIMA™ Labs, Inc. (Minneapolis, Minn.).

Preparation Method A

Appropriate amounts of PVAP and PVP, equivalent to a 2:1 weight ratio, were dissolved in minimum volumes of an aqueous ammonium hydroxide solution (28% v/v) and water, respectively, and then mixed. To the resulting mixture, ibuprofen, equal to the amount of PVAP used, was dissolved and then 0.1N HCl solution was added drop wise until the pH of the solution was 1.0. The white solid precipitate was filtered, washed with water, and then vacuum dried.

Preparation Method B

PVAP and PVP were separately dissolved in ethanol. Appropriate volumes of the resulting PVAP and PVP solutions, equivalent to a 2:1 weight ratio of PVAP and PVP, were then mixed. An immediate precipitation of a gummy solid occurred. The mixture was refluxed for an hour at boiling temperature and then filtered hot. The gummy solid was washed with hot ethanol and then dried under vacuum. Six grams of the dried solid and 4.0 g. of ibuprofen powder were then suspended in 10 ml of water. To this, an aqueous ammonium hydroxide solution (28% v/v) was added drop wise until a clear solution was obtained. The resulting solution was then treated with 0.1N HCl until the supernatant showed a pH of 1.0. The white solid precipitate was filtered, washed with water, and then vacuum dried.

Drug Content Analysis

About 25–50 mg of the entrapped ibuprofen granules were accurately weighed and dissolved in a minimum volume of a 4:1 (v/v) mixture of methylene chloride and methanol. To the clear solution, 50 ml of acetonitrile was added. The resulting suspension was stirred for 30 min., centrifuged, and then filtered directly into a 250 ml volumetric flask. The residue left at the bottom of the centrifuge tube was resuspended in 50 ml acetonitrile, centrifuged, and filtered into the same volumetric flask. The pooled drug solution was diluted to the 250 ml mark with acetonitrile and then analyzed by high performance liquid chromatography (HPLC) using a Shimadzu's SCL-6 chromatograph equipped with a SIL-6A autoinjector, a SPD-6A pump, a SPD-6AV ultraviolet-visible detector, a SCL-6A system controller, and a CR5A data processor. The drug was eluted on an Econosil $C_{18}$ analytical column (Alltech, State College, Pa.) using the mobile phase consisting of 60% acetonitrile and 40% 0.01M potassium monophosphate solution. The flow rate was set at 1.0 ml/min., and the detection was made at 200 nm.

Infrared Spectroscopy

The Fourier-transform infrared (FT-IR) spectra of products were obtained as KBr pellets on a Nicolet 5DXB infrared spectrophotometer.

Scanning Electron Microscopy

The samples were loaded on a stub with liquid graphite and then coated with gold followed by a layer of carbon for four min. and Emitech K550 coater SEM photographs were then taken on a Hitachi S-4000 scanning microscope using Polaroid® films.

Powder X-ray Diffraction

The powder X-ray diffraction (XRD) measurements were conducted on a Philips PW 1710 X-ray diffractometer using a monochromatic $Cuk_\alpha$ radiation and a scanning rate of 3° 2θ/min. over a 2θ range of 10–30°2θ.

Thermal Analysis

Thermogravimetric analysis (TGA) and differential scanning calorimetric (DSC) studies were performed on a Perkin Elmer 7 series thermal analysis system under a constant purge of nitrogen over a temperature range of 40–300° C. The heating rate used was 5° C./min. The DSC system was calibrated using indium, a reference standard, prior to analysis of samples.

Preparation of Chewable Tablets

The entrapped granules containing 39.06% ibuprofen were used in the preparation of tablets. Appropriate amounts of the granules and the cherry vehicle, corresponding to 200 mg of ibuprofen per 668 mg of tablet, were accurately weighed and then mixed in a glass jar. Tablets were prepared on a Carver press at a compression pressure of 2000 lbs. using a 13 mm die and punches and a dwell time of 60 seconds.

For comparison purposes, reference tablets containing cherry vehicle, drug, and lactose/corn starch mixture, PVP, PVAP, or a 2:1 physical mixture of PVAP-PVP, were also prepared. The amounts of various components used in each formulation are listed in Table 1. Except for Tablet formulation I, which was prepared by the wet granulation method, all other tablet preparations were by made direct compression of the respective powder mixture. In the wet granulation method, a solution of starch in water was added to the mixture of lactose and ibuprofen until a moist mass was obtained. The latter was passed through a 20-mesh screen the then dried in an oven first at 45° C. for an hour and at room temperature overnight. It was then passed through a 60-mesh screen, mixed with cherry vehicle and then compressed. Each tablet was weighed about 668 mg and contained 200 mg ibuprofen. The same tooling set and the compression conditions as was used for the PVAP-PVP complex were employed.

The hardness of tablets was measured using a Schleuniger 2E hardness tester (model 2E/106).

TABLE 1

Compositions of Chewable Ibuprofen Tablets

| Ingredient | Tablet Composition | | | | |
|---|---|---|---|---|---|
| | I[a] | II | III | IV | V |
| Ibuprofen | 200 mg | 200 mg | 200 mg | 200 mg | — |
| PVP-PVAP complex | — | — | — | — | 512 mg[b] |
| PVP | — | 312 mg | — | — | — |
| PVAP | — | — | 312 mg | — | — |
| PVAP:PVP[c] (2:1) | — | — | — | 312 mg | — |
| Cherry vehicle | 156 mg | 156 mg | 156 mg | 156 mg | 156 mg |
| Lactose | 162 mg | — | — | — | — |
| Corn starch | 150 mg | — | — | — | — |
| Tablet weight | 668 mg | 668 mg | 668 mg | 668 mg | 668 mg |
| Hardness, kp | 5.7 | >20 | 18 | >20 | 7.1 |

[a]Prepared by the wet granulation method
[b]Contained 200 mg ibuprofen
[c]Physical mixture Release Studies The dissolution of drug was studied in pH 1.2 and 7.4 buffer solutions according to the USP basket method using a VanderKamp 600 six-spindle dissolution tester (VanKel Industries, Inc., Chatam, N.J.). The stirring speed was set at 150 rpm, and the temperature of the dissolution medium was maintained at 37° C. The release of drug in pH 1.2 buffer medium was monitored for 3 hours and in pH 7.4 buffer solution for 6 hours. Five milliliters of samples were withdrawn at 15, 30, 60, 120, 180, 300, and 360 min. The removed samples were immediately replaced with an equal volume of the respective buffer solution. The samples were filtered through a 0.45 µfilter membrane and then analyzed by HPLC using conditions described above.

Results

Physicochemical approaches such as flocculation, coagulation, and precipitation of polymers from their aqueous or non-aqueous dispersions/solutions by drugs, a bivalent or trivalent metal salt or an appropriate organic solvent, have been widely used for taste masking of drugs. In the instant invention, a new method that involves in situ complexation between PVAP and PVP has been used to entrap ibuprofen, a water insoluble, bitter tasting anti-inflammatory drug, to produce palatable granules suitable for use in the development of chewable tablets. The entrapment procedure involves dissolving the drug in an ammonical solution containing a 2:1 weight ratio of PVAP and PVP, followed by adjusting the pH of the solution to about 1. The low pH of the solution ensues complexation between PVAP and PVP, concomitant with the precipitation and subsequent entrapment of ibuprofen, producing an insoluble product. The yield of the entrapped product, irrespective of whether the PVAP-PVP complex that had been previously prepared in ethanol or produced in situ directly from PVAP and PVP was employed, was 85–90%. The percent drug content in the granules, determined in two different batches of the product by HPLC, varied between 91% and 98%, of the theoretical amounts, indicating a near quantitative entrapment of ibuprofen by the method.

Characterization of Entrapped Ibuprofen Granules

The FT-IR spectra of free drug, PVAP-PVP complex, and PVAP-PVP entrapped ibuprofen granules are shown in FIG. 1. As is evident, the infrared spectrum of the entrapped granules shows peaks that are representative of free drug and the PVAP-PVP complex. In the carbonyl frequency region, the peak at 1721 $cm^{-1}$ in the spectrum of entrapped ibuprofen granules is attributed to the C=O stretching vibration belonging to the carboxylic group in ibuprofen and to the acetate and phthalate moieties in PVAP. The corresponding peak in the spectra of free drug and PVAP-PVP complex appears at 1721 and 1724 $cm^{-1}$, respectively. The band at 1657 $cm^{-1}$ in the spectrum of PVAP-PVP complex is assigned to the cyclic amide of the pyrrolidone ring in PVP. In the case of entrapped ibuprofen granules, this peak appears at 1659 $cm^{-1}$. The lack of a significant shift in the carbonyl frequency in the spectrum of granules with respect to the corresponding peak in the spectra of free drug and complex suggests that the drug entrapment process of the instant invention is a physical phenomenon. The broad, strong peak at 3450 $cm^{-1}$ in the spectrum of PVAP-PVP complex is due to the bound O—H stretching vibration. In the case of entrapped granules, the intensity of this peak is nearly half of that observed for the complex, suggesting that the entrapment of ibuprofen partially disrupted the interaction between hydroxyl groups.

Figure 2:
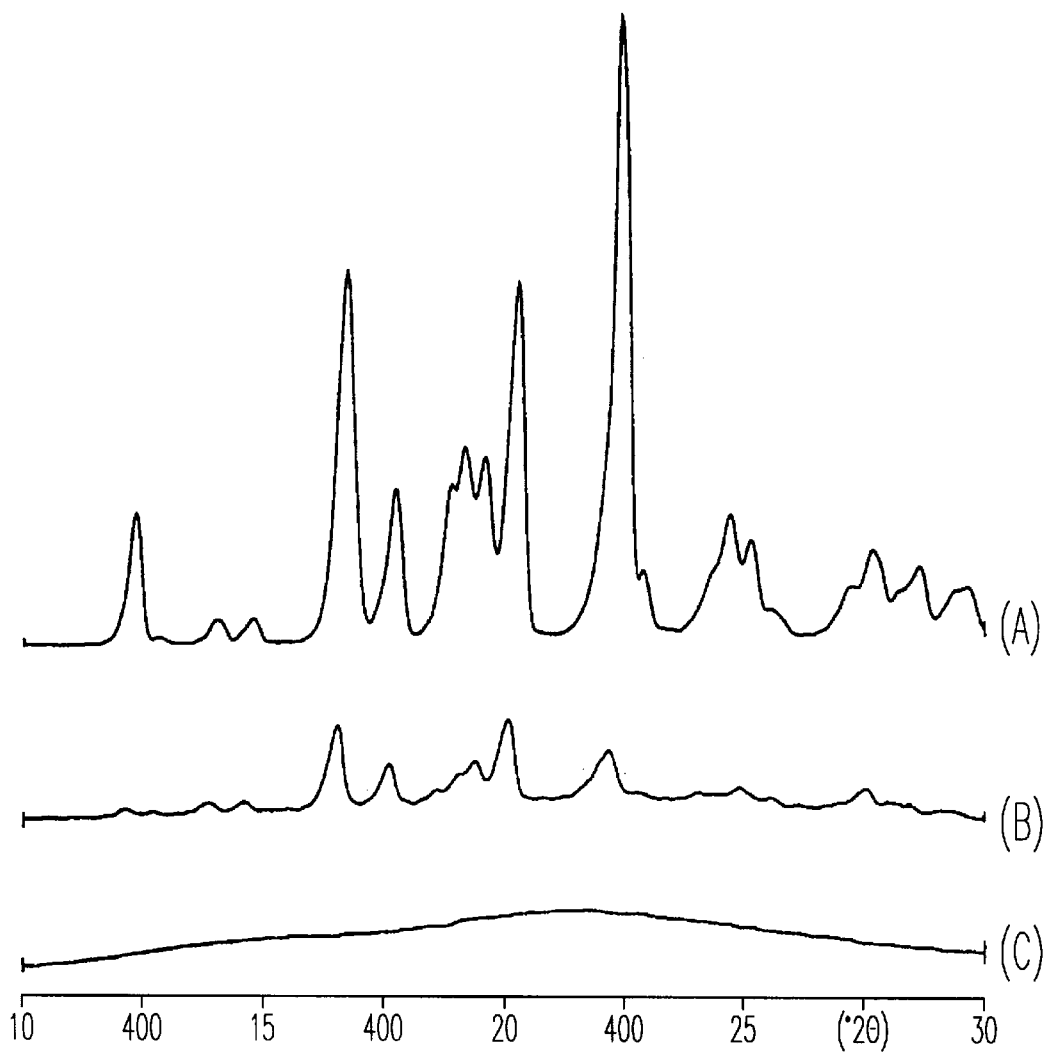
FIG. 2 shows powder X-ray diffractograms of (A) ibuprofen, (B) PVAP-PVP entrapped ibuprofen granules, and (C) PVAP-PVP complex.

FIG. 2 shows the XRD patterns of free drug, PVAP-PVP complex, and the entrapped ibuprofen granules. The free drug showed several diffraction peaks, whereas the PVAP-PVP complex displayed two diffuse halos (from 10° 2θ to 17.5° 2θ and from 17.50° 2θ to 30° 2θ), indicating that the former is a highly crystalline material and the latter is an amorphous substance. The XRD pattern of the entrapped granules appears similar to that of the free drug except for that the diffraction peaks are much smaller in intensity. A comparison of the intensity of various peaks shows that the peak at 22° 2θ, the strongest reflection in the diffractogram of the free drug, appears only as a small peak in the XRD patter of granules. These results suggest that the lowering of the pH to ensue in situ complexation between PVAP and PVP causes partial amorphinization of ibuprofen. The different peak intensity order seen, compared to that of free drug, could be due to the different polymorphic form of ibuprofen or because of different crystal orientations during the analysis. Sekizaki et al. Solid state interaction of ibuprofen with polyvinylpyrrolidone, Chem. Pharm. Bull., 43, 988–993 (1995) studied the effect of moisture content on the crystallinity of ibuprofen in the presence of PVP. They reported that ibuprofen became amorphous when merely mixed with dry PVP. When mixed with moist PVP, the crystallinity of ibuprofen increased with increasing moisture content.

Figure 3:
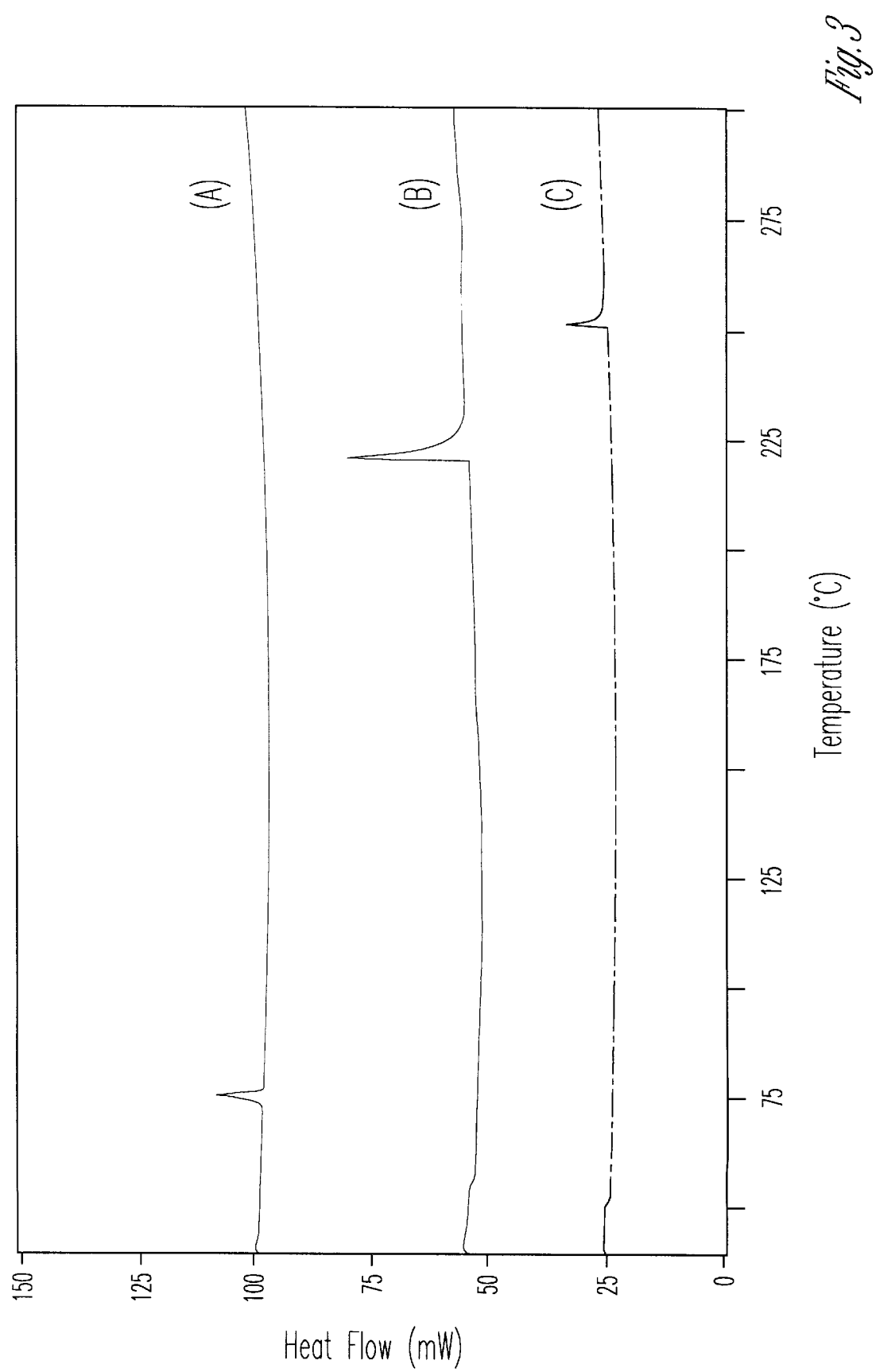
FIG. 3 shows DSC curves of (A) ibuprofen, (B) PVAP-PVP entrapped ibuprofen granules, and (C) PVAP-PVP complex.
Figure 4:
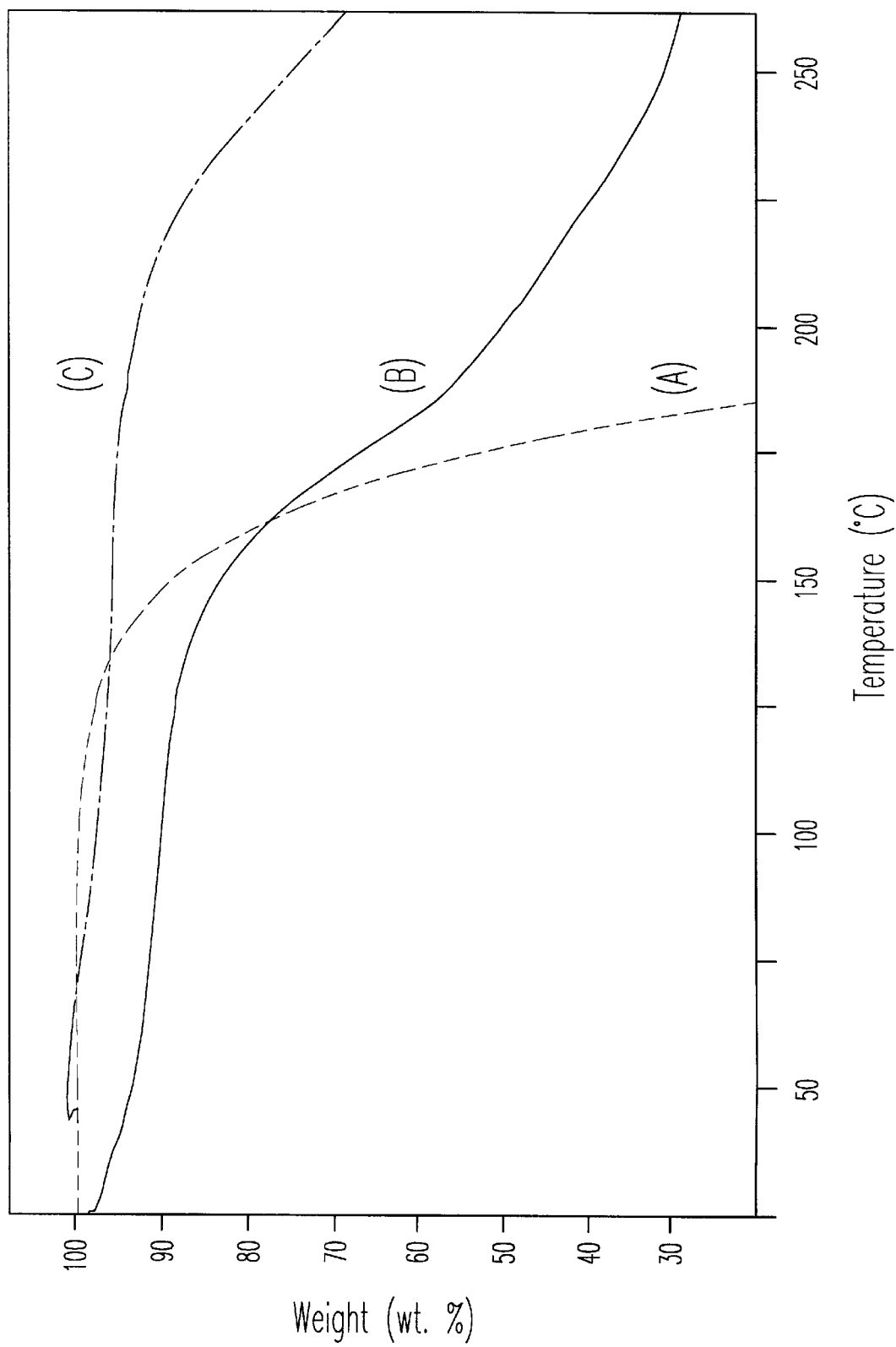
FIG. 4 shows TGA curves of (A) ibuprofen, (B) PVAP-PVP entrapped ibuprofen granules, and (C) PVAP-PVP complex.

The DSC and TGA thermograms of ibuprofen, PVAP-PVP complex and the entrapped ibuprofen granules are reproduced in FIGS. 3 and 4, respectively. The endothermic signal at 76.5° C. and a sharp decline in weight at 140° C. observed for the free drug are due to melting an decomposition of the sample, respectively. The PVAP-PVP complex, in contrast, exhibited an endothermic peak at 251° C. and a decrease in weight due to degradation at about 212° C. In the case of entrapped granules, the endothermic peak appeared at 217° C. and the decomposition of the sample began at 151° C. These results suggest that the endothermic peaks observed for PVAP-PVP and the entrapped granules are due to the decomposition product. The absence of the melting endotherm at 76.5° C. due to ibuprofen in the DSC thermogram of the entrapped granules is attributed to the amorphinization of ibuprofen during the entrapment process. The absence of the melting endothermic peak at 76.5° C. also suggests that the proportion of crystalline form of ibuprofen present in the granules is very small, below the detection limit of DSC. The lower decomposition temperature observed for the granules compared to that of the complex is attributed to the presence of ibuprofen.

Release Studies

The compositions of the various tablet formulations used in the release study are presented in Table 1. Tablets prepared using the entrapped ibuprofen granules or developed by the wet granulation method were nearly three times less strong than those containing PVP, PVAP, or a physical mixture of PVAP and PVP. The entrapped ibuprofen granules were palatable, and the tablets prepared using them provided a good mouth feel afterwards.

Figure 5:
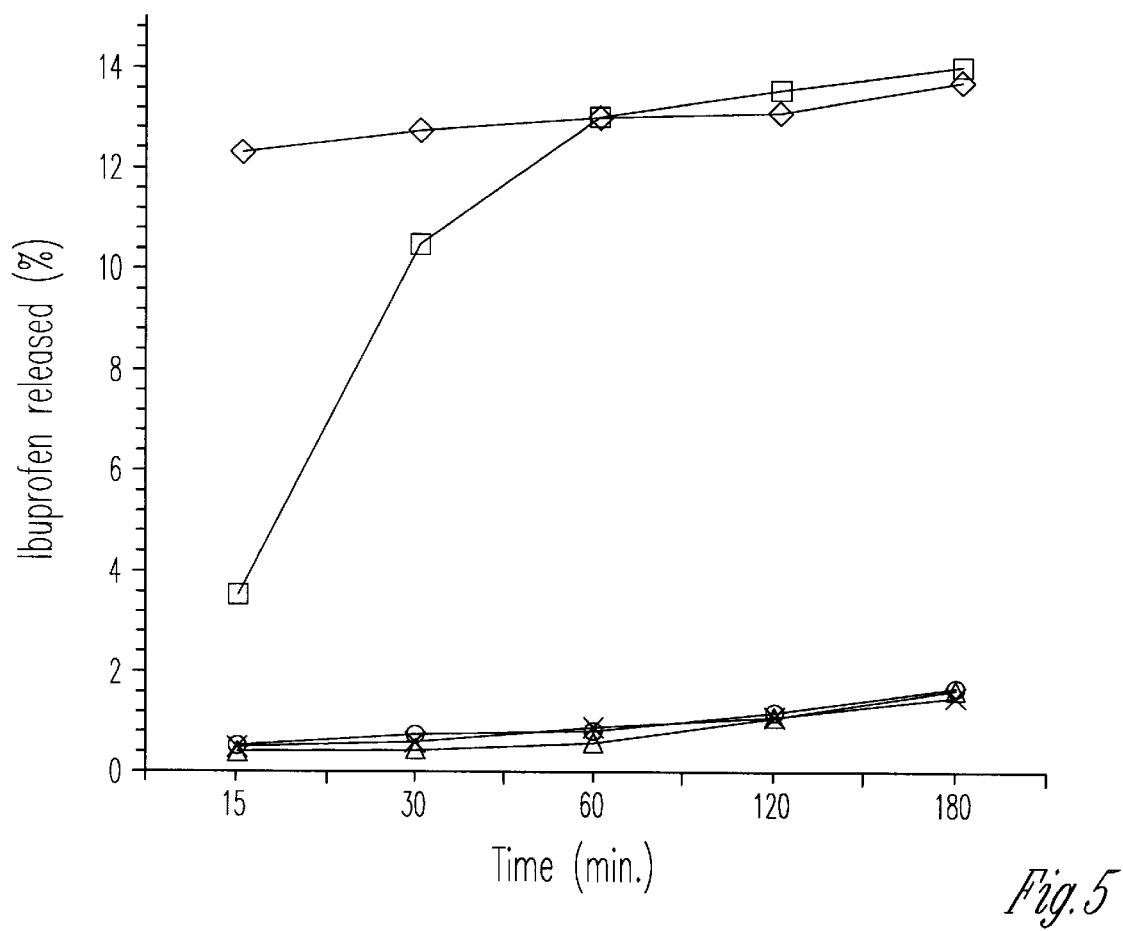
FIG. 5 shows release profiles of ibuprofen from various chewable tablet formulations in pH 1.2 buffer.

The release characteristics of various chewable tablet formulations in pH 1.2 and 7.4 buffer solutions are shown in FIGS. 5 and 6, respectively. In pH 1.2 buffer, Tablet I disintegrated rapidly, Tablet II stayed at the top of the basket, Tablet III stayed in the middle, Tablet IV freely moved up and down in the basket, and Tablet V sat at the bottom of the basket during the test period. There was no noticeable change in the size and surface smoothness of Tablets IV and V after three hours. Tablet II, in contrast, developed pores and showed a rough surface. Tablet III also showed rough surface but the extent of roughness was less than that observed with Tablet III. The percentage amounts of drug released form Tablets I and II in three hours were 13%. Tablet III, IV, and V, in contrast, showed a release of less than 2% of ibuprofen over the same time period. The higher dissolution of ibuprofen from Tablets I and II can be attributed to the solubilizing properties of corn starch/lactose and PVP.

In pH 7.4 buffer solution, Tablet I disintegrated rapidly and released 100% of drug in about ten minutes. This was followed by Tablet II, which released 95% of drug in three hours. Tablet III showed a slower release profile initially compared to that of Tablet II ($t_{1/2}$80 min. versus 60 min., respectively). But, after about three hours, both Tablets II and III released ibuprofen at about the same rates. Tablet IV, which was prepared using a 2:1 (w/w) physical mixture of PVAP and PVAP, showed the slowest release profile. The times to release 50% and 90% of drug from Tablet IV were about two hours and five hours respectively. Tablet V, which contained the entrapped ibuprofen granules, in contrast, released 50% of drug in 80 min., the same time as was seen with Tablet II. After 80 min., however, the release was slower, causing the remaining drug to release over a period of five hours. The relatively slower release of ibuprofen from Tablet IV than from Tablets II and III suggests that PVAP and PVP when used together probably form a slowly dissolving complex upon hydration. Studies are in progress to investigate the interaction between PVP and PVAP in aqueous solutions ranging in pH between 5 and 8.

The results presented show that in-situ complexation between a free-hydroxyl polymer and PVP can be used to entrap water insoluble, bitter tasting drugs to produce palatable granules suitable for use in the development of a sustained release chewable tablet formulation.

It should be appreciated that minor dosage and formulation modifications of the composition and the ranges expressed herein may be made and still come within the scope and spirit of the present invention.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

What is claimed is:

1. A polymer complex for entrapping drug granules comprising:

a complex of polyvinyl acetate phthlate (PVAP); and polyvinylpyrrolidine (PVP);

said PVAP-PVP complex having bands at about 1657 $cm^{-1}$ and 1724 $cm^{-1}$ in the spectrum of the PVAP-PVP complex.

2. A polymer complex according to claim 1 whereby the polymer and the polyvinylpyrrolidine are present in a weight ratio that affords the maximum yield.

3. A polymer complex according to claim 1 wherein the polymer is polyvinyl acetate phthlate (PVAP).

4. A polymer complex according to claim 3 whereby the polymer and the polyvinylpyrrolidine are present in a weight ratio ranging from about 4:1 to about 1:4 PVAP to PVP.

5. A polymer complex according to claim 1 further including a flavoring agent.

6. A polymer complex according to claim 1 further including one or more pharmaceutical excipients selected from the group consisting of binder, lubricant, disintegrant, coloring agent, flavoring agent, and diluent.

7. A polymer-entrapped drug comprising:

a drug that is insoluble in organic solvent, but soluble or suspendable in an alkaline solution and insoluble in aqueous acidic solutions;

a complex of polyvinyl acetate phthlate (PVAP); and polyvinylpyrrolidine (PVP);

said PVAP-PVP complex having bands at about 1657 $cm^{-1}$ and 1724 $cm^{-1}$ in the spectrum of the PVAP-PVP complex.

8. A polymer-entrapped drug according to claim 7 wherein the polymer and the PVP are present in a weight ratio that affords the maximum yield of the complex.

9. A polymer-entrapped drug according to claim 7 wherein the drug is a bitter-tasting drug.

10. A polymer-entrapped drug according to claim 9 wherein the drug is an NSAID.

11. A polymer-entrapped drug according to claim 10 wherein the drug is ibuprofen.

12. A polymer-entrapped drug according to claim 7 further including one or more pharmaceutical excipients selected from the group consisting of binder, lubricant, disintegrant, coloring agent, flavoring agent, and diluent.

13. A polymer-entrapped drug according to claim 7 wherein the complex is insoluble at acidic pH.

14. A polymer-entrapped drug comprising:

a drug that is insoluble in organic solvent, but soluble or suspendable in an alkaline solution and insoluble in aqueous acidic solutions;

said drug being entrapped in a complex of polyvinyl acetate phthlate (PVAP) and polyvinylpyrrolidine (PVP);

said PVAP-PVP complex having bands at about 1657 $cm^{-1}$ and 1724 $cm^{-1}$ in the spectrum of the PVAP-PVP complex.

* * * * *

(12) EX PARTE REEXAMINATION CERTIFICATE (6297th)
United States Patent
Kumar

(10) Number: US 6,372,259 C1
(45) Certificate Issued: Jul. 15, 2008

(54) PALATABLE, SUSTAINED RELEASE DRUG GRANULES

(75) Inventor: Vijay Kumar, Coralville, IA (US)

(73) Assignee: University of Iowa Research Foundation, Iowa City, IA (US)

Reexamination Request:
No. 90/008,672, Sep. 7, 2007

Reexamination Certificate for:
Patent No.: 6,372,259
Issued: Apr. 16, 2002
Appl. No.: 09/437,449
Filed: Nov. 10, 1999

(51) Int. Cl.
*A61K 9/14* (2006.01)
*A61K 9/50* (2006.01)

(52) U.S. Cl. ......................................... 424/497; 424/489
(58) Field of Classification Search ........................ None
See application file for complete search history.

(56) References Cited

PUBLICATIONS

Development of a Chewable Ibuprofen Tablet Formulation, Tianrun Yang, Vijay Kumar & Yuwo Yang, Pharmaceutics Division, University of Iowa College of Pharmacy, Nov. 18, 1998 American Association of Pharmaceutical Scientist Poster Session (attached hereto as Exhibit B).

Development of a Chewable Ibuprofen Tablet Formulation, Tianrun Yang, Vijay Kumar & Yuwo Yang, vol. 1 No. 1 Nov. 16, 1998, American Association of Pharmaceutical Scientists Annual Meeting Abstracts (attached hereto as Exhibit C).

Interpolymer Complexation, I. Preparation and Characterization of a Polyvinyl Acetate Phthalate–Polyvinylpyrrolidone (PVAP–PVP) Complex, Vijay Kumar, T. Yang & Y. Yang, 188 International Journal of Pharmaceutics 221–32, (1999) (attached hereto as Exhibit D).

Kumar, V. et al. "Interpolymer complexation, II. Entrapment of Iburofen by in–situ complexation between polyvinyl acetate phthalate (PVAP) and polyvinylpyrrolidone (PVP) and development of a chewable tablet formulation", Paper No. 2, 2007, 33 pages.

*Primary Examiner*—Gary L Kunz

(57) ABSTRACT

A means and method for manufacturing palatable drug granules using a polymer having at least one free carboxyl group and PVP is described. This is achieved by (1) dissolving/suspending a drug in an aqueous solution of polymers and subsequently adjusting the pH of the solution to an acidic pH or (2) suspending a drug in an organic solution of one of the aforementioned polymers and then adding the other polymer solution, with constant agitation. The polymers form a complex and consequently entraps the drug and produce palatable drug granules that are suitable for preparing sustained release pharmaceutical dosage forms (powders, suspension, tablets, chewable tablets).

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–14 is confirmed.

\* \* \* \* \*